United States Patent
Eberle et al.

(10) Patent No.: US 8,157,746 B2
(45) Date of Patent: Apr. 17, 2012

(54) DEVICE FOR CUTTING OUT TISSUE SPECIMENS

(75) Inventors: Walter Eberle, Bernried (DE); Peter Hloch, Kochel (DE); Christoph Hundt, Munich (DE); Alois Rainer, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1220 days.

(21) Appl. No.: 11/272,187

(22) Filed: Nov. 10, 2005

(65) Prior Publication Data

US 2006/0122641 A1    Jun. 8, 2006

(30) Foreign Application Priority Data

Nov. 15, 2004   (EP) .................................... 04027137
Sep. 16, 2005   (EP) .................................... 05020235

(51) Int. Cl.
  *A61B 10/00*   (2006.01)
  *A61B 17/32*   (2006.01)
  *A61B 17/14*   (2006.01)

(52) U.S. Cl. ......... 600/564; 606/167; 606/172; 606/184

(58) Field of Classification Search .......... 600/562–567; 606/1, 167, 184, 185, 172, 170; 604/265
See application file for complete search history.

(56) References Cited

U.S. PATENT DOCUMENTS

| | | | |
|---|---|---|---|
| 3,990,451 A |   | 11/1976 | Gibbs |
| 5,325,857 A | * | 7/1994 | Nabai et al. .................... 600/567 |
| 5,394,886 A | * | 3/1995 | Nabai et al. .................... 600/567 |
| 5,827,199 A | * | 10/1998 | Alexander ..................... 600/564 |
| 2002/0111563 A1 | * | 8/2002 | Hall .............................. 600/566 |
| 2003/0082797 A1 |   | 5/2003 | Rastorgoueff et al. |
| 2004/0116942 A1 |   | 6/2004 | Feller |

FOREIGN PATENT DOCUMENTS

EP   1293167 A2   3/2003

OTHER PUBLICATIONS

Greene, Optimizing Mold Parameters, Chapter 4, MFGT 144, Sep. 20, 1999.*
Yokoyama, T: Prion Disease Research Center, National Institute of Animal Healt, "Retest of Prionics WESTERN for the first Japanese BSE case" [online], Aug. 13, 2003 [retrieved on Jun. 23, 2009]. Retrieved from the Internet:<URL:http://niah.naro.affrc.go.jp./disease/bse/retest_prionics.html>.

* cited by examiner

*Primary Examiner* — Brian Szmal
(74) *Attorney, Agent, or Firm* — Dinsmore & Shohl LLP

(57) ABSTRACT

The present invention relates to a device for separating a tissue part from brain material, the device comprising a circular blade which continues as the wall of a cylindrical or substantially cylindrical hollow body, at the end of which a grid is arranged perpendicular to the cylinder axis. The invention further relates to the use of the device in a method for separating a tissue part from brain material and to a kit containing one or more devices according to the invention.

19 Claims, 4 Drawing Sheets

DEVICE FOR CUTTING OUT TISSUE SPECIMENS

RELATED APPLICATIONS

This application claims priority to European patent application EP 04027137.1 filed Nov. 15, 2004 and to European patent application EP 05020235.7 filed Sep. 16, 2005.

FIELD OF THE INVENTION

The present invention relates to a cutting device with which a quantitatively defined tissue specimen can be removed from a larger tissue specimen or tissue mass, preferably brain tissue obtained post mortem from resected brainstem. A preferred embodiment is a cutting device for one-off use. The invention further concerns a method for removing quantitatively defined tissue specimens from a larger tissue specimen or tissue mass using the cutting device.

BACKGROUND OF THE INVENTION

After slaughter, cows over a certain age are presently examined for BSE (bovine spongiform encephalopathy, prion infection) with the aid of an immunological test, e.g., the PRIONICS-Check LIA, PRIONICS-Check WESTERN or PrionScreen BSE assays (PRIONICS is a registered trademark of Prionics AG, Switzerland). The cadaver is released for further processing and allowed to enter the human food chain upon obtaining a negative test result. Part of the brainstem (medulla oblongata), preferably the obex region (FIG. 1), is used as starting material for removal of a tissue specimen with which the test is carried out. Part of the brainstem is removed in the slaughterhouse. By way of the foramen magnum, i.e., the large opening on the posterior of the skull through which the spinal cord emerges, the obex and adjacent areas are removed using a specially shaped spoon and are introduced into a special container. In the container, the brain material is taken to a test laboratory where the actual specimen for establishing a prion infection is removed.

A number of test systems presently available on the market require the analysis to be carried out with a defined quantity of specimen material. The quantity is generally determined by weighing. To do this, manual operations have to be conducted in which potentially infectious material is handled under stringent biological safety conditions. Particularly with a view to safety at work, it is desirable to limit the operations using unsealed brain material. In concrete terms, it would be advantageous to be able to determine the quantity more quickly and more easily since, in this way, more specimens can be fed to a test system per unit of time. This would have a positive impact on the specimen throughput attainable in the laboratory.

In the state of the art there are devices known which were designed for taking samples from tissue or a tissue specimen. However, the state of the art has certain disadvantages.

EP 1 293 167 discloses a cutting device for biopsies comprising a hollow needle with a circular blade. A grid inside the needle limits the amount of tissue which can be taken up by the cavity of the needle. Also inside the needle, between the grid and the opening of the needle a thin wire is stretched between two opposite points at the inner wall of the needle. After the device is pushed into a tissue specimen the needle is twisted, whereby the tissue portion located between the grid and the wire is cut from the remaining tissue specimen. Suction is applied to retain the cut portion of tissue at the grid, thereby allowing removal of the cut portion from the remaining tissue specimen.

US 2004/0116942 discloses a device for extraction of follicular units from a donor area, for the purpose of transplantation into balding areas of the scalp. The device comprises a cylindrical punch to which a perforator is affixed, and a grid as a guard member aimed at containing successfully extracted hair follicles. The punch is described as being a standard biopsy punch with a diameter of 1 mm, corresponding to the size of a single target follicular unit. The punch is used to make a first circular incision around the hair follicle. The perforator is used to make a second, deeper incision to weaken the structural integrity of the surrounding connective tissue without damaging the hair follicle. Subsequently, the follicular unit is extracted using suction. In the device the grid prevents the follicular unit to enter the suction means and be eventually lost.

Other devices for removing tissue parts are disclosed in U.S. Pat. No. 3,990,451 and US 2003/082797.

SUMMARY OF THE INVENTION

It was an object of the present invention to make available a simple device which can be produced as a disposable and with which a quantitatively defined tissue specimen can be obtained from potentially infectious brain material quickly and reliably and with reduced manual work. A further object of the invention was to particularly minimize the risk of injury during the sampling process as well as the risk of contamination. A further object was to make available a method in which the number of manual steps leading to a quantitatively defined tissue specimen is reduced. A further object of the invention was to make available a method in which the steps leading to a quantitatively defined tissue specimen are simplified and speeded up.

According to the invention, the problem was solved by provision of a device for cutting out a tissue part from brain material (hereinafter also called cutting device). A first preferred embodiment of the invention is a device for separating a tissue part from brain material and shown in FIG. 1 and FIG. 2, characterized in that said device is a hollow, tube-shaped entity comprising (i) at the front end a circular blade (10) which continues as the wall of a cylindrical or substantially cylindrical body (20), at the end of which a grid (30) is arranged perpendicular to the cylinder axis; (ii) a cylindrical or substantially cylindrical shaft (40) which is joined with the cylindrical body (20) on the other side of the grid (30); (iii) at the rear end a cylindrical or substantially cylindrical handle (60) which is joined with the shaft by a widening part (50) with the surface of a truncated cone whose ends are circular, the end of the smaller circle diameter starting flush on the rear end of the shaft, and the end with the larger circle diameter starting flush on the handle. A further preferred embodiment of the invention is a mould for injection molding of a device according to the invention. A further preferred embodiment of the invention is the use of a mould according to the invention for manufacturing a device according to the invention. A further preferred embodiment of the invention is the use of a device according to the invention for separating a tissue part from brain material. A further preferred embodiment of the invention is a method for separating a tissue part from brain material, comprising the following steps: (a) preparing a section of brainstem containing the obex region, said section of brainstem being placed with the ventral face on a smooth, fixed support; followed by (b) placing the blade of a device according to the invention vertically on a predetermined site of the obex region; followed by (c) pressing the blade in the vertical direction into the brain material while executing rotation movements, until the blade has made complete contact with the support; followed by (d) withdrawing the device from the section of brainstem and removing the tissue part contained in it. A further preferred embodiment of the invention is a kit containing one or more devices according to the invention, instructions for use, and packaging material containing the aforementioned items.

DETAILED DESCRIPTION OF THE INVENTION

Figure 1:
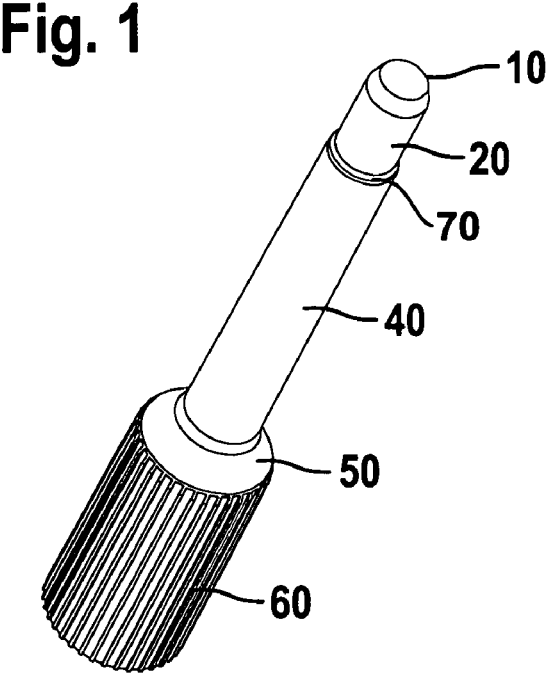
FIG. 1: Device according to the invention, exterior view. Reference number (10) circular blade; (20) cylindrical or substantially cylindrical body; (40) shaft; (50) widening part; (60) handle; (70) further widening part connecting (20) and (40).
Figure 2:
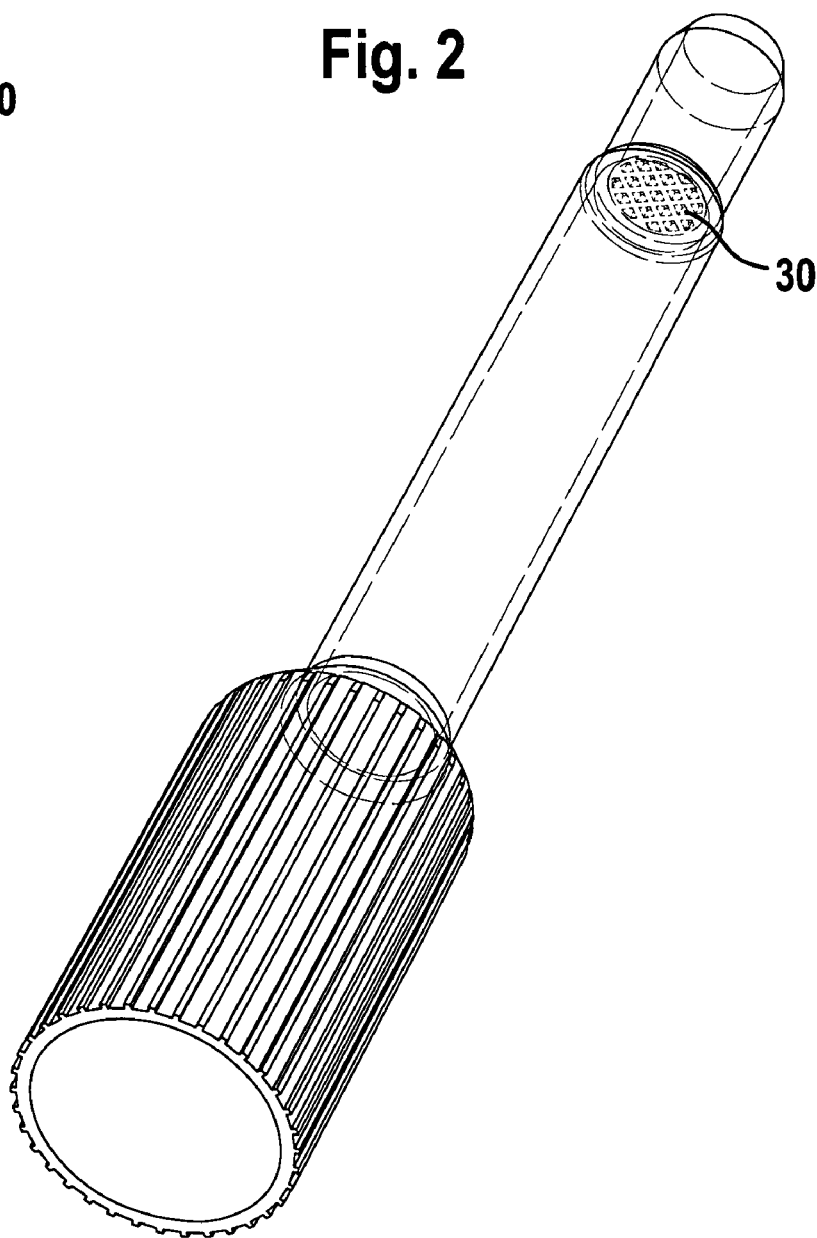
FIG. 2: Preferred cutting device according to the invention, interior features. Reference number (30) grid.
Figure 3:
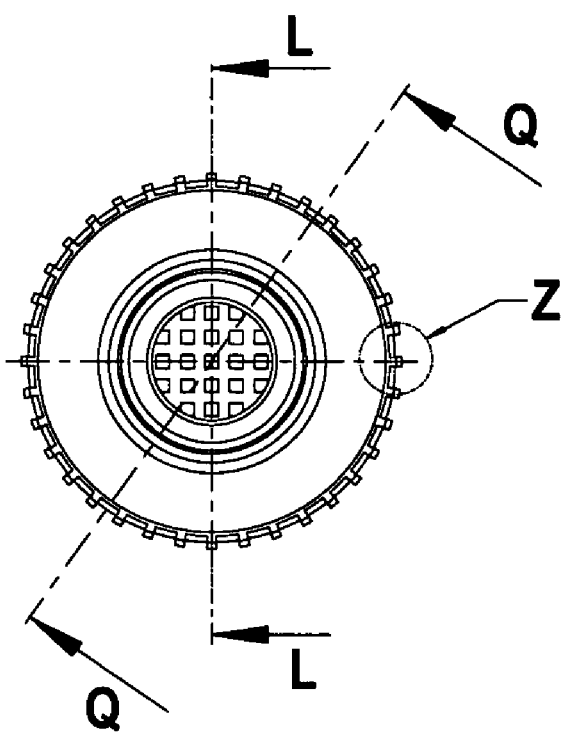
FIG. 3: View along the central longitudinal axis towards the grid; the view is taken through the handle of the device shown in FIG. 1 and FIG. 2, the point of the observer lying on the central longitudinal axis. L-L and Q-Q define two different axes of cross section. Z marks the zone which is depicted enlarged in FIG. 6.
Figure 6:
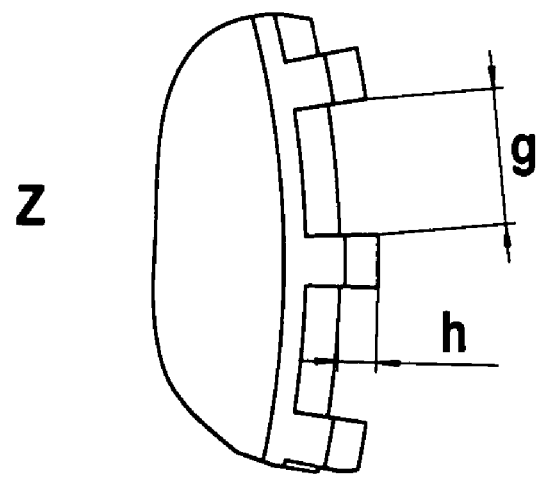
FIG. 6: Enlarged section of the grip. Distances are given for a particularly preferred embodiment with an assumed measuring tolerance of [±0.09 mm]; (g) 1.1 mm; (h) 0.3 mm.
Figure 4:
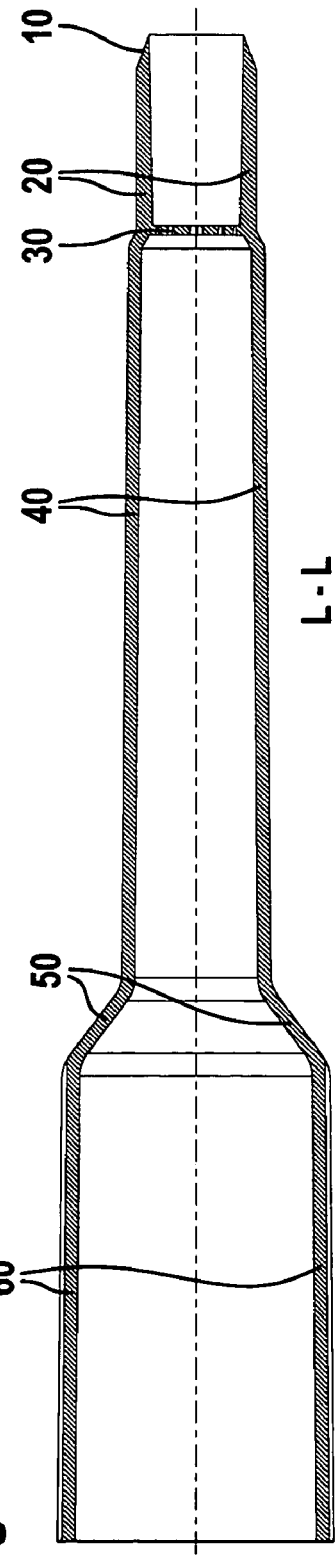
FIG. 4: This figure shows the L-L cross section of a device according to the invention along the central longitudinal axis. Reference number (10) cutting edge; (20) wall of the cylindrical or substantially cylindrical body; (30) grid; (40) shaft; (50) widening part; (60) handle.
Figure 5:
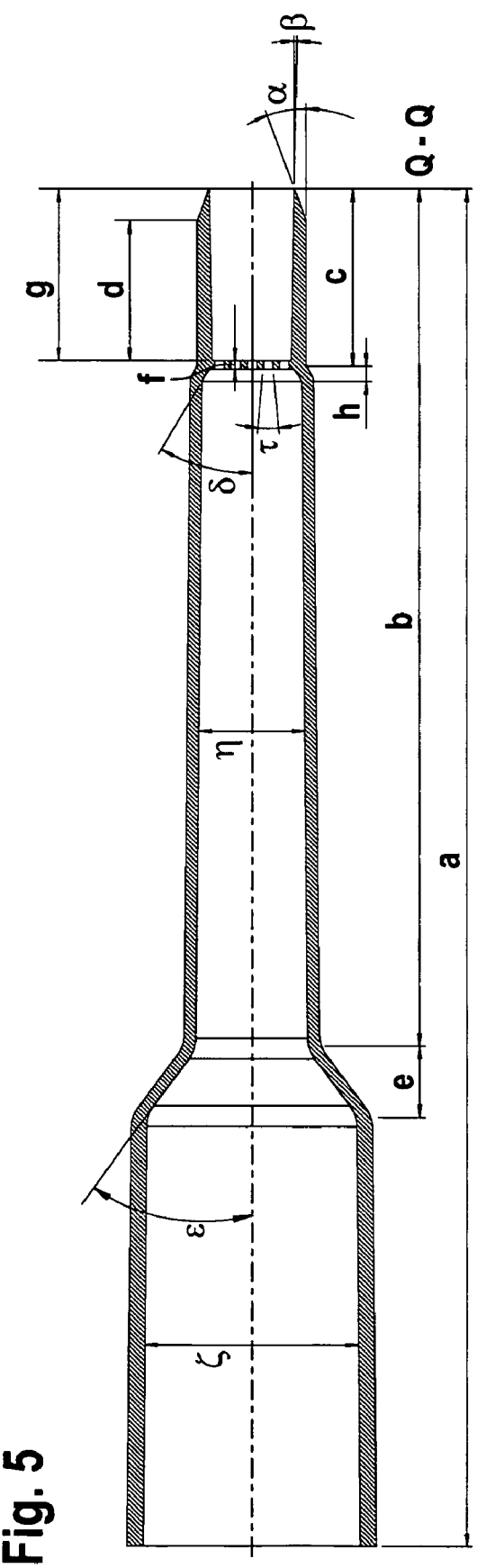
FIG. 5: This figure shows the Q-Q cross section of a device according to the invention along the central longitudinal axis. Angles are marked with Greek letters, distances with roman letters. Angles and distances are given for a particularly preferred embodiment of the invention. Angles are measured in degrees (°) whereby an angle of 1° is understood as ⅟₃₆₀ of the circle circumference. The assumed measuring tolerance is ±1°. (α) 20°; (β) 1°; (τ) 10°; (δ) 30°; (η) 1°; (ε) 36°; (ζ) 1°. Distances are given with an average measuring tolerance of ±0.1 mm. (a) 95 mm; (b) 60 mm; (c) 12.4 mm; (d) 10 mm; (e) 5 mm; (f) 0.6 mm; (g) 12 mm.

According to the invention, the cutting device comprises a circular blade which continues as the wall of a cylindrical or substantially cylindrical hollow body, at the end of which a grid is arranged perpendicular to the cylinder axis. The cutting device also comprises a shaft which continues the cylinder axis on the other side of the grid in the direction of the longitudinal axis (extending from the cutting edge to the grid). The shaft can be used as a handle when using the device. In a preferred embodiment, the shaft is a hollow body which is open at both ends. A particularly preferred embodiment of the invention is a device for separating a tissue part from brain material and shown in FIG. 1 and FIG. 2, characterized in that said device is a hollow, tube-shaped entity comprising (i) at the front end a circular blade (10) which continues as the wall of a cylindrical or substantially cylindrical body (20), at the end of which a grid (30) is arranged perpendicular to the cylinder axis; (ii) a cylindrical or substantially cylindrical shaft (40) which is joined with the cylindrical body (20) on the other side of the grid (30); (iii) at the rear end a cylindrical or substantially cylindrical handle (60) which is joined with the shaft by a widening part (50) with the surface of a truncated cone whose ends are circular, the end of the smaller circle diameter starting flush on the rear end of the shaft, and the end with the larger circle diameter starting flush on the handle. Optionally, the device according to the invention further comprises (iv) a smooth fixed support against which the circular blade can be pressed.

In a preferred embodiment, the grid (30) contains at least 5 elements with openings. It is preferred to have 15 to 30 elements with openings. It is also preferred that the width of each grid bar is between 0.2 mm and 1 mm, very much preferred 0.4 mm.

In a preferred embodiment, the shaft comprises a cylindrical or substantially cylindrical hollow body which starts on the cylinder of the blade on the other side of the grid. In a further preferred embodiment, the shaft has a further widening part (70) with the surface of a truncated cone whose ends are circular, the end with the smaller circle diameter starting flush on the cylinder of the blade on the other side of the grid, and the end with the larger diameter starting flush on a cylindrical or substantially cylindrical hollow body.

In a further preferred embodiment, the shaft comprises (a) a first cylindrical hollow body which starts flush on the cylinder of the blade on the other side of the grid and continues this cylinder in the direction of the longitudinal axis, (b) a widening part with the surface of a truncated cone whose ends are circular, the end with the smaller circle diameter starting on the cylinder of (a) on the other side of the grid, and the end with the larger diameter starting flush on (c) a cylindrical or substantially cylindrical hollow body.

In a further preferred embodiment the outside diameter of the shaft is at least equal to the outside diameter of the cylindrical body (20). Also preferred, the outside diameter of the shaft is up to 1.5 times wider than the outside diameter of the cylindrical body (20). The shaft (40) has a length between 20 mm and 100 mm.

In a preferred embodiment the front part of the shaft (40) is joined with the cylindrical body (20) on the other side of the grid (30) by a further widening part (70) with the surface of a truncated cone whose ends are circular, the end of the smaller circle diameter starting flush on the cylindrical body (20) on the other side of the grid (30), and the end with the larger circle diameter starting flush on the front part of the shaft (40). The grid can be adjoined to or be the internal structure of the further widening part (70). In a preferred embodiment said further widening part measures between 1 mm and 5 mm in length and has a widening angle of between 5° and 45°, relative to the wall of the cylindrical body (20). Particular preference is given to a widening angle of approximately 30°. In this regard, an angle of 1° is understood as ⅟₃₆₀ of the circle circumference.

The handle of the device provides grip for manual operation thus allowing quick, precise and safe handling. In a preferred embodiment the outside diameter of the handle (60) at the rear end is between 1.5 to 10 times wider than the outside diameter of the cylindrical body (20). More preferred, the outside diameter of the handle (60) at the rear end is between 15 mm and 60 mm, even more preferred between 15 mm and 20 mm, even more preferred about 17 mm.

Also preferred, the outside surface of the handle (60) is corrugated longitudinally.

FIG. 1, FIG. 2, FIG. 3, FIG. 4, FIG. 5, and FIG. 6 show details of embodiments of the cutting device according to the invention.

Since the cutting device is provided for working with potentially infectious brain material, it is preferably intended to be used only once by the user (i.e., is designed as a disposable item). Disposable items can be advantageously produced in large numbers by injection molding. Thus, a further preferred embodiment of the invention is a mould or a plurality of moulds for injection molding of a device according to the invention. Another preferred embodiment is the use of said mould for manufacturing a device according to the invention.

When practicing injection molding it is preferred to shape hollow tube-like structures not exactly cylindrical but substantially cylindrical. In some preferred cases, the interior of the cutting part of the device is substantially cylindrical. This is to be understood as meaning that the interior tapers from the cutting edge towards the grid. This arrangement is advantageous if the cutting device is made of a plastic material by means of injection molding. The angle of taper of the cylindrical void of each the cylindrical body (20), the cylindrical shaft (40), and the handle (60) is typically between about 0.5° and about 10°, preferably between about 0.5° and about 5°, particularly preferably about 1°. In one embodiment, the cylindrical void of the cylindrical shaft (40) is tapered from a first end of the shaft to a second end of the shaft. In another embodiment, the cylindrical void of the cylindrical shaft (40) is tapered from the second end of the shaft to the first end of the shaft.

In a preferred embodiment the inner wall of the cylindrical body (20) forms the surface of a truncated cone whose ends are circular, the end of the smaller circle diameter facing the grid (30), and the end with the larger circle diameter being the circle formed by the blade, whereby the diameters of the smaller circle and the larger circle are selected such that they result in a truncated cone with an opening angle of between 0.1° and 5°.

In a further preferred embodiment the inside wall of the handle forms the surface of a truncated cone whose ends are circular, the end of the smaller circle diameter facing the widening part (50), whereby the diameters of the smaller circle and the larger circle are selected such that they result in a truncated cone with an opening angle of between 0.1° and 5°. In a further preferred embodiment the inside wall of the shaft forms the surface of a truncated cone whose ends are circular, the end of the smaller circle diameter facing the grid (30) or the further widening part (70), whereby the diameters of the smaller circle and the larger circle are selected such that they result in a truncated cone with an opening angle of between 0.1° and 5°.

Various starting materials used in injection molding are well known to the skilled person. Because of the required blade function of the cutting edge, hard plastics are more preferable to soft plastics. A plastic material from the group of polycarbonates is preferred for this purpose, particularly preferably the plastic called MAKROLON (Bayer AG, Germany). The most preferred material is MAKROLON 2458.

As will be described below, the cutting device can be used to cut out a tissue part as cylindrical core from a larger tissue mass. The preferred distance between blade edge and grid corresponds substantially to the thickness of the material that is to be cut through. The preferred diameter of the circle formed by the blade and thus of the diameter of the interior will depend on the required quantity of specimen.

Figure 7:
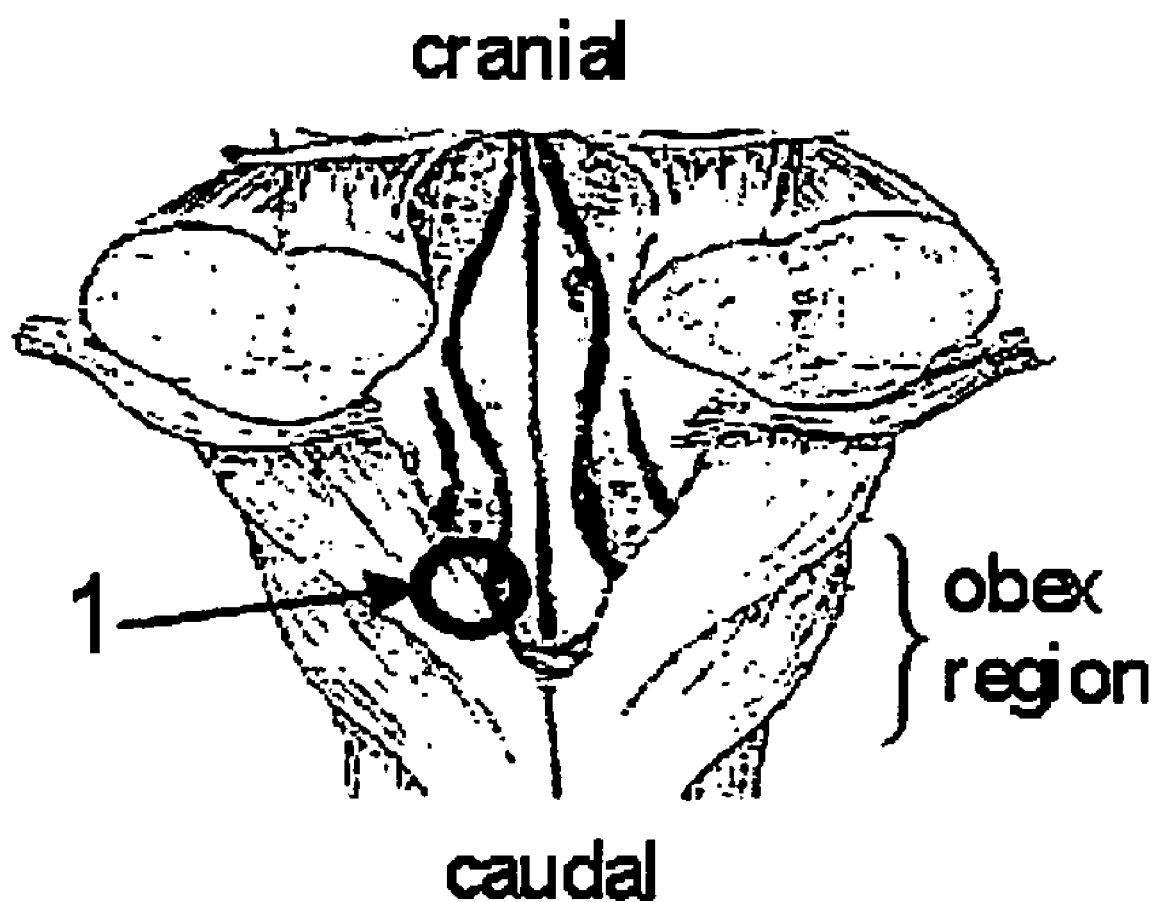
FIG. 7: Dorsal view of the section of a bovine brainstem containing the obex region. Cranial: towards skull; caudal: towards spinal cord.

A particularly preferred embodiment of the cutting tool involves cutting out a cylindrical or substantially cylindrical tissue core from the area of the brainstem referred to as the obex, said tissue core being cut from the obex in the dorsoventral direction at the site (removal site) indicated by reference number (1) in FIG. 7, as will be described below.

The brainstem sections from which tissue cores are to be removed as specimens usually come from cattle which are about two years old. But the sizes of the obex region of animals above 2 years of age differ only slightly. Consequently, it is sufficient for a given purpose, for example for taking specimens from brainstem sections of cows which are between 2 and 8 years old, to make the cutting device available in a single defined size (related to the tissue core that is to be produced with it).

The volume of the interior of the cylindrical body (20) from the blade edge to the grid is usually larger than the volume of the tissue core being cut out with the cutting device. Nevertheless, the volume of the interior is preferably adapted to the quantity of brain material needed for the purposes of the test.

For removal of tissue cores, the distance between blade edge and grid is therefore preferably between 5 mm and 20 mm, particularly preferably between 10 mm and 15 mm, very particularly preferably about 12 mm. The diameter of the circle formed by the blade is preferably between 3 mm and 10 mm, particularly preferably between 5 mm and 7 mm, very particularly preferably 5.8 mm.

The preferred wall thickness of the blade wall and of the grid elements is preferably between 0.3 mm and 2 mm, particularly preferably between 0.5 mm and 1 mm, still more preferably between 0.6 mm and 0.8 mm. The edge of the circular blade is sharp, the cutting edge tapering from the outside inwards at an angle of between 10° and 30°. A preferred angle of taper is between 15° and 25°, particular preference being given to an angle of taper of about 20°.

The wall thickness of the handle is of importance only to the extent that it has to ensure that the cutting device can be handled without breaking. A preferred wall thickness in the handle area is between 0.5 mm and 4 mm.

A further preferred embodiment of the invention is the use of a device according to the invention for separating a tissue part from brain material. To remove a cylindrical or substantially cylindrical tissue core of defined quantity, in other words a quantitatively defined specimen, the section of brainstem is placed with its ventral face on a horizontal, fixed support so that the dorsal face is directed upwards, corresponding to the view of the dorsal face of the medulla oblongata shown in FIG. 1. Further information on the site of removal can be found at http://niah.naro.affrc.go.jp/disease/bse/retest_prionics.html. At the site indicated by (1), the circular blade of the cutting device is pressed vertically into the brain material while executing rotation movements until the blade has made complete contact with the support. In this way, a cylindrical or substantially cylindrical tissue mass (tissue core) is separated from the obex region. This procedure is usually done manually.

The grid arranged in the cutting device on the one hand limits the tissue material taken up and on the other hand allows air to escape from the interior of the space formed by the circular blade.

With the aid of tweezers, the section of brainstem is now pushed in the direction of the widening part (50) and in this way, in some circumstances, remaining tough connections of tissue parts to the tissue core are severed. The cutting device is withdrawn from the brainstem section and the tissue core is removed with the aid of tweezers from the interior and transferred to a test container.

At this step, the grid arranged in the punching tool has a further function. When the tissue core is being removed, it avoids the development of an underpressure which would hold back the soft tissue and lead to its tearing. In this way, soft or fragile tissue specimens can also be removed without increased risk of contamination. In addition, while the grid does not limit the amount of tissue being cut out from the brainstem, it prevents the tissue core from moving further inwards when manipulated with forceps.

After use, the cutting device is disinfected and disposed of. For this purpose, the cutting device is preferably autoclaved. The small size of the cutting device according to the invention means that the amount of waste material to be disposed of is small. Another or else subsequent preferred way of disposal involves incineration of the cutting device.

The example, publications, and figures further explain the invention, and the patent claims define the scope of its protection. The described methods are to be understood as examples which, even after modifications, describe the subject of the invention.

Specific Embodiments

EXAMPLE 1

Removing a Tissue Specimen from the Obex of a Slaughtered Cow

In the slaughterhouse, the medulla oblongata or a part containing the obex region is withdrawn through the foramen magnum with the aid of a specially shaped spoon and stored in a special container. In the laboratory, the device according to the invention is used to cut out an approximately cylindrical piece of tissue and to remove the latter from the section of brainstem. The cut-out piece of tissue is then removed from the device using tweezers and forwarded for analysis in order to test if appropriate for the presence of infectious prions.

When removing the piece of tissue, particular care is taken to ensure that the removed piece of tissue is free of blood clots.

What is claimed is:

1. A device for manually cutting tissue by hand, comprising:
   a cylindrical shaft having (i) a first end, (ii) a second end, (iii) an inner cylindrical void positioned between the first and second ends, the inner cylindrical void having (i) a first void end and (ii) a second void end;
   a handle directly attached to the first end of the shaft by a first widening part of the shaft;
   a cylindrical body attached to the second end of the shaft by a second widening part of the shaft so that the longitudinal axis of the cylindrical body is coaligned with the longitudinal axis of the cylindrical shaft, the cylindrical body having a hollow interior;
   a circular blade defined on a free end of the cylindrical body; and
   a grid positioned in the hollow interior of the cylindrical body adjacent the second end of the cylindrical shaft,
   wherein the hollow interior of the cylindrical body tapers from the circular blade towards the grid, and
   wherein the shaft between the first and second widening parts defines another handle such that the handle and the shaft are configured to be gripped by hand to manually cut the tissue.

2. The device of claim 1, wherein the taper of the cylindrical void has a taper angle from 0.5° to 10°.

3. The device of claim 1, wherein the taper of the cylindrical void has a taper angle from about 0.5° to 5°.

4. The device of claim 1, wherein the taper of the cylindrical void has a taper angle of 1°.

5. The device of claim 1, wherein the cylindrical body has an outer circumference that is less than the outer circumference of the cylindrical shaft, and the hollow interior of the cylindrical body defines an inner cylindrical void.

6. The device of claim 1, wherein the taper of the hollow interior of the cylindrical body has a taper angle from 0.5° to 10°.

7. The device of claim 1, wherein the taper of the hollow interior of the cylindrical body has a taper angle from 0.5° to 5°.

8. The device of claim 1, wherein the taper of the hollow interior of the cylindrical body has a taper angle of 1°.

9. The device of claim 1, wherein the handle has a cylindrical shape and has an outer circumference that is greater than the outer circumference of the cylindrical shaft;
   the handle defines an inner cylindrical void having a (i) a first void end and (ii) a second void end; and
   the inner cylindrical void of the handle is tapered from the first void end to the second void end.

10. The device of claim 9, wherein the taper of the cylindrical void of the handle has a taper angle from 0.5° to 10°.

11. The device of claim 9, wherein the taper of the cylindrical void of the handle body has a taper angle from 0.5° to 5°.

12. The device of claim 9, wherein the taper of the cylindrical void of the handle has a taper angle of 1°.

13. A device for manually cutting tissue by hand, comprising:
   a cylindrical shaft having a first end and a second end;
   a handle directly attached to the first end of the shaft by a first widening part of the shaft; and
   a cylindrical body attached to the second end of the shaft by a second widening part of the shaft so that the longitudinal axis of the cylindrical body is coaligned with the longitudinal axis of the cylindrical shaft,
   wherein the cylindrical body has an outer circumference that is less than the outer circumference of the cylindrical shaft, the cylindrical body defines an inner cylindrical void having a grid therein, a first void end and a second void end, and the inner cylindrical void of the cylindrical body is tapered from the first void end to the second void end, and
   wherein the shaft between the first and second widening parts defines another handle such that the handle and the shaft are configured to be gripped by hand to manually cut the tissue.

14. The device of claim 13, wherein the taper of the cylindrical void of the cylindrical body has a taper angle from 0.5° to 10°.

15. The device of claim 13, wherein the taper of the cylindrical void of the cylindrical body has a taper angle from 0.5° to 5°.

16. The device of claim 13, wherein the taper of the cylindrical void of the cylindrical body has a taper angle of 1°.

17. A device for manually cutting tissue by hand, comprising:
   a cylindrical hollow shaft having a first end and a second end;
   a handle directly attached to the first end of the cylindrical hollow shaft by a first widening part of the shaft;
   a cylindrical body attached to the second end of the shaft by a second widening part of the shaft so that a cylinder axis of the cylindrical body is coaligned with a cylinder axis of the cylindrical hollow shaft, the cylindrical hollow body having a hollow interior and a free end with a cutting edge; and
   a grid positioned in the hollow interior of the cylindrical body perpendicular to the cylinder axis of the cylindrical body and adjacent the second end of the cylindrical shaft, the grid having elements defining openings, wherein the hollow interior of the cylindrical body tapers from the cutting edge towards the grid, and the cutting edge tapers outside inwardly from an exterior surface of the cylindrical body to the free end, and wherein the shaft between the first and second widening parts defines another handle such that the handle and the shaft are configured to be gripped by hand to manually cut the tissue.

18. The device for cutting tissue according to claim 17 wherein the handle is corrugated longitudinally.

19. The device for cutting tissue according to claim 17 wherein the first and second widening parts each have a widening angle of between 5° to 45°.

* * * * *

UNITED STATES PATENT AND TRADEMARK OFFICE
CERTIFICATE OF CORRECTION

PATENT NO.        : 8,157,746 B2                                           Page 1 of 1
APPLICATION NO.   : 11/272187
DATED             : April 17, 2012
INVENTOR(S)       : Walter Eberle et al.

It is certified that error appears in the above-identified patent and that said Letters Patent is hereby corrected as shown below:

On the title page, correct item [30] as follows:
Foreign Application Priority Data:

"(EP).....................04027137" should read -- (EP).....................04027137.1 --; and
"(EP).....................05020235" should read -- (EP).....................05020235.7 --.

Signed and Sealed this
Second Day of October, 2012

David J. Kappos
*Director of the United States Patent and Trademark Office*